(12) United States Patent
Pays et al.

(10) Patent No.: US 8,211,415 B2
(45) Date of Patent: Jul. 3, 2012

(54) EASILY REMOVABLE WATERPROOF COSMETIC CARE AND/OR MAKEUP COMPOSITION COMPRISING AT LEAST ONE LATEX OR PSEUDOLATEX

(75) Inventors: Karl Pays, Saint-Maurice (FR); Yohann Bichon, Maisons-Alfort (FR); Sandrine Olivier-Mabilais, L'Hay les Roses (FR)

(73) Assignee: L'Oreal, Paris (FR)

( * ) Notice: Subject to any disclaimer, the term of this patent is extended or adjusted under 35 U.S.C. 154(b) by 1016 days.

(21) Appl. No.: 11/248,471

(22) Filed: Oct. 13, 2005

(65) Prior Publication Data

US 2006/0078520 A1    Apr. 13, 2006

Related U.S. Application Data

(60) Provisional application No. 60/618,590, filed on Oct. 15, 2004.

(30) Foreign Application Priority Data

Oct. 13, 2004  (FR) ...................................... 04 10824

(51) Int. Cl.
*A61K 8/92* (2006.01)
(52) U.S. Cl. ..................................................... 424/70.7
(58) Field of Classification Search .................. None
See application file for complete search history.

(56) References Cited

U.S. PATENT DOCUMENTS

| 4,423,031 | A | 12/1983 | Murui et al. |
| 4,887,622 | A | 12/1989 | Gueret |
| 5,156,911 | A | 10/1992 | Stewart |
| 6,024,946 | A | 2/2000 | Dubief et al. |
| 6,126,929 | A | 10/2000 | Mougin |
| 6,287,543 | B1 | 9/2001 | Terren et al. |
| 6,946,123 | B2 | 9/2005 | De La Poterie et al. |
| 2003/0118542 | A1 | 6/2003 | Auguste et al. |
| 2003/0170196 | A1* | 9/2003 | Orsoni et al. ............... 424/70.17 |
| 2003/0171479 | A1* | 9/2003 | Lennon ........................ 524/501 |
| 2004/0091447 | A1 | 5/2004 | Pays et al. |
| 2004/0156887 | A1* | 8/2004 | Auriou ........................... 424/450 |
| 2006/0013790 | A1* | 1/2006 | Shimizu .................... 424/70.12 |
| 2006/0130248 | A1* | 6/2006 | Pays et al. ....................... 8/406 |

FOREIGN PATENT DOCUMENTS

| EP | 0 119 333 A1 | 9/1984 |
| EP | 0 628 304 A1 | 12/1994 |
| EP | 0 663 161 A1 | 7/1995 |
| EP | 0 792 603 A1 | 9/1997 |
| EP | 0 847 752 A1 | 6/1998 |
| EP | 1 152 022 A1 | 11/2001 |
| EP | 1 396 259 A2 | 3/2004 |
| FR | 2 605 505 A1 | 4/1988 |
| FR | 2 701 198 A1 | 8/1994 |
| FR | 2 761 959 A1 | 10/1998 |
| FR | 2 774 996 A1 | 8/1999 |
| FR | 2 785 801 A1 | 5/2000 |
| FR | 2 792 190 A1 | 10/2000 |
| FR | 2 792 618 A1 | 10/2000 |
| FR | 2 796 529 A1 | 1/2001 |
| FR | 2 815 850 A1 | 5/2002 |
| FR | 2 844 196 A1 | 3/2004 |
| FR | 2 859 101 A1 | 3/2005 |
| JP | A-6-510273 | 11/1994 |
| JP | A-2004-277403 | 10/2004 |
| WO | WO 95/35089 A1 | 12/1995 |
| WO | WO 96/36309 | 11/1996 |
| WO | WO 98/18431 * | 5/1998 |
| WO | WO 99/26445 A1 | 5/1999 |
| WO | WO 99/52499 A1 | 10/1999 |
| WO | WO 01/01935 A1 | 1/2001 |
| WO | WO 01/01936 A1 | 1/2001 |
| WO | WO 01/19333 A1 | 3/2001 |
| WO | WO 02/47622 A2 | 6/2002 |
| WO | WO 2004/060273 A2 | 7/2004 |

OTHER PUBLICATIONS

Griffin, W., "Calculation of HLB Values of Non-Ionic Surfactants", vol. 5, pp. 249-256, Atlas Powder Company, Wilmington, DE, May 14, 1954.
Kirk-Othmer, Encyclopedia of Chemical Technology, 3$^{rd}$ Edition, vol. 22, pp. 333-432, Wiley, 1979.
ISO Standard 11357-3, 1999 (with Jul. 2005 Amendment).
Van de Hulst, H.C., "Light Scattering by Small Particles", Chapters 9 and 10, pp. 114-130 and 131-170, Wiley, New York, 1957.
Boutevin, et al., "Study of Morphological and Mechanical Properties of PP/PBT Blends", Polymer Bulletin 34, pp. 117-123, 1995.
Rangarajan, et al., "Morphology of Semicrystalline Block Copolymers of Ethylene-(Ethylene-alt-propylene)", Macromolecules, vol. 26, pp. 4640-4645, American Chemical Society, 1993.
Richter, et al., Polymer Aggregates with Crystalline Cores: The System Polyethylene-Poly(ethylenepropylene), Macromolecules, vol. 30, pp. 1053-1068, American Chemical Society, 1997.
Hamley, I.W., "Crystallization in Block Copolymers", Advances in Polymer Science, vol. 148, pp. 113-137, Leeds, U.K., 1999.
Intelimer Polymers, Landec IP22 (Ref 4-97), 6 pages, 1998.
Van de Hulst, H.C., Light Scattering by Small Particles, Chapters 9 and 10, Wiley, New York (1957), pp. 114-171.

* cited by examiner

*Primary Examiner* — Brian Gulledge
(74) *Attorney, Agent, or Firm* — Oliff & Berridge, PLC

(57) ABSTRACT

The present invention relates to a composition for making up and/or caring for keratin materials, the composition having an aqueous continuous phase and comprising at least one aqueous dispersion of particles of a polymer other than a copolymer obtained by condensation of diethylene glycol, cyclohexanedimethanol, isophthalic acid and sulfoisophthalic acid, at least one wax, at least one polyelectrolyte and at least one salt, the polymer being present in a solids content of greater than or equal to 5% by weight relative to the total weight of the composition.

17 Claims, No Drawings

EASILY REMOVABLE WATERPROOF COSMETIC CARE AND/OR MAKEUP COMPOSITION COMPRISING AT LEAST ONE LATEX OR PSEUDOLATEX

BACKGROUND

This non provisional application claims the benefit of French Application No. 04 10824 filed on Oct. 13, 2004 and U.S. Provisional Application No. 60/618,590 filed on Oct. 15, 2004, each of which is herein incorporated by reference in its entirety.

There are in practice essentially two types of mascara formulation, firstly mascaras with an aqueous continuous phase, known as "emulsion mascaras", which are in the form of an emulsion of waxes in water, and, secondly, mascaras with a solvent or oil continuous phase, which are anhydrous or have a low content of water and/or of water-soluble solvents, known as "waterproof mascaras", which are formulated in the form of a dispersion of waxes in non-aqueous solvents. There are also certain mascaras that are in the form of emulsions of waxes in water, which are also termed "waterproof". The latter compositions are characterized by the presence of at least one latex or pseudolatex, i.e. a colloidal suspension of a film-forming polymer, which imparts the waterproof nature.

These "waterproof" mascaras comprising at least one latex or pseudolatex may give rise to difficult makeup removal with certain makeup removers, in particular makeup removers that are mainly water-based or water-soluble, especially aqueous solutions. The makeup removal is thus generally performed using special makeup removers based on oils or organic solvents. However, these makeup removers may be irritant to the eyes, may especially cause stinging or may leave a veil on the eyes, or alternatively may leave an uncomfortable greasy residual film on the skin around the eyes (eyelids).

There is thus a need for cosmetic makeup compositions that are capable of showing both good water resistance and an improved ability to be removed, including with the usual makeup removers.

Documents FR 2 785 801, EP 1 152 022, FR 2 774 996, and WO 95/35089 describe thickening compositions, known as "thickening latices", "thickeners" or "inverse latices".

Documents FR 2 785 801 and FR 2 774 996 especially disclose compositions comprising an aqueous phase, an oily phase, an emulsifier of O/W (oil-in-water) type and an emulsifier of W/O (water-in-oil) type, and also a branched or crosslinked anionic polyelectrolyte based on a monomer containing a strong acid function.

Document WO 99/52499 mainly describes lipsticks comprising a sodium polyacrylate, for the purpose of producing a volumizing effect.

SUMMARY

The present invention relates to cosmetic compositions for making up and/or caring for keratin materials, especially the skin, the lips and/or keratin fibres, which are capable of resisting water by means of the presence of at least one latex or pseudolatex, but which can nevertheless be easily removed.

More particularly, the compositions according to the invention may constitute a makeup product for the face, the body and/or the lips and for keratin fibres, for instance the eyelashes, the eyebrows and the hair, and more particularly an eyelash makeup product.

It may especially be a makeup composition, a transparent or coloured composition to be applied over or under a makeup, also known, respectively, as a "top coat" or a "base coat", or alternatively a composition for treating the eyelashes.

The composition according to the invention may be in the form of a product for the eyelashes, or mascara, a product for the eyebrows or a hair makeup product. The invention more especially relates to a mascara.

The present invention relates more particularly to compositions or mascaras of "waterproof" type comprising at least one latex or pseudolatex.

It has now been discovered that it is possible to obtain cosmetic compositions for making up and/or caring for keratin materials, which comprise at least one latex or pseudolatex and which are capable of combining good water resistance and improved makeup removal irrespective of the type of makeup remover.

According to a first aspect, the present invention relates to a composition for making up and/or caring for keratin materials, the said composition having an aqueous continuous phase and comprising at least one aqueous dispersion of particles of a polymer other than a copolymer obtained by condensation of diethylene glycol, cyclohexanedimethanol, isophthalic acid and sulfoisophthalic acid, at least one wax, at least one polyelectrolyte and at least one salt, the said polymer being present in a solids content of greater than or equal to 5% by weight relative to the total weight of the composition.

According to a second aspect, the present invention relates to a composition for making up and/or caring for keratin materials, the said composition having an aqueous continuous phase and comprising at least one aqueous dispersion of particles of a polymer, at least one polyelectrolyte in a solids content of greater than 1% by weight relative to the total weight of the composition, the said polyelectrolyte being other than gum arabic, and at least one surfactant with an HLB of greater than or equal to 6, the said polymer being present in a solids content of greater than or equal to 5% by weight relative to the total weight of the composition.

According to a third aspect, the present invention relates to a composition for making up and/or caring for keratin materials, the said composition having an aqueous continuous phase and comprising at least one aqueous dispersion of particles of a polymer not comprising an ionizable monomer, at least one polyelectrolyte, and at least one surfactant with an HLB of greater than or equal to 6, the said polymer being present in a solids content of greater than 5% by weight relative to the total weight of the composition.

According to a fourth aspect, the present invention relates to a composition for making up and/or caring for keratin materials, the said composition having an aqueous continuous phase and comprising at least one aqueous dispersion of particles of a polymer, at least one wax, and at least one polyelectrolyte in a solids content of greater than or equal to 0.4% by weight relative to the total weight of the composition, the said polyelectrolyte being other than gum arabic, the said composition containing at least one salt when the said polymer is present in a solids content of greater than or equal to 2% by weight relative to the total weight of the composition, and the said composition being different from the following composition:

| | |
|---|---|
| Sulfopolyester (copolymer obtained by condensation of diethylene glycol, cyclohexanedimethanol, isophthalic acid and sulfoisophthalic acid) as active material | 18 g |
| Wax microdispersion | 31 g |

-continued

| | |
|---|---|
| AMPS/acrylamide copolymer | 1.5 g |
| Gum arabic | 1 g |
| Amorphous silica microspheres | 3 g |
| Simethicone | 0.19 g |
| Propylene glycol | 5 g |
| Ethanol | 5 g |
| Pigments | 7 g |
| Preserving agents | qs |
| Sodium hydroxide | qs pH = 7 |
| Water | qs 100 g, | the wax microdispersion having the following composition:

| | |
|---|---|
| Carnauba wax | 27 g |
| Polyoxyethylenated (30 EO) glyceryl monostearate | 6.75 g |
| Ethanol | 10 g |
| Water | qs 100 g |

According to a fifth aspect, the present invention relates to a cosmetic process for making up and/or caring for keratin materials, comprising at least one step of applying to the keratin materials any of the compositions as defined above.

According to a sixth aspect, the present invention relates to a made-up support comprising a makeup that may be obtained according to the process as defined above.

According to an seventh aspect, the present invention relates to the use of the combination of at least one polyelectrolyte and of at least one surfactant with an HLB of greater than or equal to 6 at 25° C., as an additive for jointly imparting good water resistance and ease of removal to a cosmetic composition having an aqueous continuous phase comprising at least one aqueous dispersion of particles of a polymer.

As emerges from the examples below, the compositions according to the invention show the technical advantages outlined above.

DETAILED DESCRIPTION OF EMBODIMENTS

The term "cosmetic composition having an aqueous continuous phase" means a system capable of becoming diluted or dispersed on contact with water.

The term "volatile organic oil or solvent" means an organic oil or solvent (or non-aqueous medium) capable of evaporating on contact with the skin in less than one hour, at room temperature and atmospheric pressure. The volatile oil is a volatile cosmetic oil, which is liquid at room temperature, especially having a non-zero vapour pressure at room temperature and atmospheric pressure, in particular having a vapour pressure ranging from 0.13 Pa to 40 000 Pa ($10^{-3}$ to 300 mmHg) and preferably ranging from 1.3 Pa to 8000 Pa (0.01 to 60 mmHg).

In the context of the present invention, the term "keratin materials" includes the skin, the lips, the nails, the hair, the eyelashes and the eyebrows.

In the context of the present invention, the term "keratin fibres" especially means the hair, the eyelashes and the eyebrows. Furthermore, the making up of the skin especially includes the making up of the body, the hands, the neck or the face.

The composition according to the invention comprises a physiologically acceptable medium, especially a cosmetically acceptable medium, i.e. a medium that is compatible in particular with keratin materials and especially keratin fibres such as the hair, the eyelashes and the eyebrows.

In the context of the present invention, the term "cosmetically acceptable" means a compound whose use is compatible with application to the keratin materials.

In general, for the sake of simplicity, and unless otherwise mentioned, the contents are indicated as solids.

Polyelectrolyte

The term "polyelectrolyte" means a macromolecular substance that has the capacity of dissociating when it is dissolved in water or in any other ionizing medium, to give at least one ion. In other words, a polyelectrolyte is a polymer comprising at least one ionizable monomer.

In particular, the polyelectrolyte may give polyions, for example polyanions, when it is dissociated in water. A polyelectrolyte may be a polyacid, a polybase, a polysalt or a polyampholyte. In the context of the invention, it is preferably a polyacid, and preferably a strong polyacid.

Preferably, the polyelectrolyte included in the cosmetic compositions according to the present invention is a branched and/or crosslinked anionic polymer.

Preferably, the polyelectrolyte is also capable of forming a gel in solution at 0.5% by weight (of solids).

Advantageously, it is also different from the polymer in aqueous dispersion.

The counterions of the polyions formed during the dissociation may be mineral or organic, of any nature.

In particular, when the polyelectrolyte is a branched or crosslinked anionic polymer, the cations may be alkali metal or alkaline-earth metal cations such as sodium or potassium, or alternatively the ammonium ion.

The sodium cation $Na^+$ is preferred, which is why it is mainly cited in the list of polyelectrolytes that follows, without this constituting any limitation to this specific counterion.

Polyelectrolytes that may be mentioned include:

the acrylamide/Na AMPS copolymer such as Simulgel 600® in emulsion form containing polysorbate 80 as surfactant and containing isohexadecane as oil phase, sold by the company SEPPIC, or alternatively Simulgel EG®, Simulgel A® and Simulgel 501® sold by the same company.

Simulgel 600® is especially described in document FR 2 785 801. It is in effect an inverse latex. The AMPS polyelectrolyte is 2-methyl-2-[(1-oxo-2-propenyl)amino]-1-propanesulfonic acid partially or totally salified especially in sodium salt or ammonium salt form to a proportion of 30 mol % to 50 mol % in the mixture comprising AMPS and also an acrylamide, which is itself present in a proportion of 50% to 70%.

crosslinked sodium starch glycolate in powder form, sodium polyacrylates such as Norsocryl S35® sold by the company Atofina, or Cosmedia SP® sold by the company Cognis, ionizable polysaccharide derivatives such as cellulose salts and sodium alginates, starch-based grafted copolymers such as the Waterlock® products (for example A-180 and G-400) from Grain Processing Corporation, polyacrylic acids of Synthalen K® type, polyacrylic acid alkyl acrylate copolymers of Pemulen® type, AMPS (polyacrylamidomethylpropanesulfonic acid partially neutralized with ammonia and highly crosslinked) sold by the company Clariant, polyoxyethylenated AMPS/alkyl methacrylate copolymers (crosslinked or non-crosslinked), sodium carboxymethylcellulose and any ionizable cellulose derivative, and mixtures thereof.

Sodium polyacrylate and acrylamide/AMPS copolymer and copolymers thereof are most particularly suitable for use in the invention. In embodiments, the polyelectrolyte is an acrylamide/2-methyl-2-[(1-oxo-2-propenyl)amino]-1-propanesulfonic acid copolymer, a polyacrylate, or copolymers thereof.

It will obviously be arranged for the polyelectrolyte content to be adjusted such that the removability is effectively improved while at the same time not being detrimental to the water resistance of the cosmetic composition.

It is understood that the amount of polyelectrolyte can vary significantly depending on the nature of the polyelectrolyte. In general, this amount is at least equal to the amount that is necessary and sufficient to give the said composition better removability. It is also termed as the effective amount.

This removability may especially be assessed by means of the test given in the examples below.

Without this constituting any limitation to the invention, the inventors have put forward the theory that the polyelectrolyte acts as a "water pump". Thus, this "water pump" role is more clearly seen when the composition is placed in contact with an aqueous phase at the time of makeup removal. During the makeup removal, the film of the cosmetic composition according to the invention becomes brittle at the surface and results in its mechanical rupture; fragmentation of the film then takes place.

The polyelectrolyte may be present in a weight content, expressed relative to the total weight of the composition, of greater than or equal to 0.05%, preferably greater than or equal to 0.1% and especially greater than or equal to 0.4%.

In particular, the polyelectrolyte may be present in the cosmetic composition in a content ranging from 0.1% to 15% by weight, especially from 0.2% to 10% by weight and more particularly from 0.3% to 5% by weight relative to the total weight of the composition.

The polyelectrolyte may also be present in the composition in a content ranging from 1% to 15% by weight, in particular from 1.5% to 10% by weight and especially from 2% to 7% by weight relative to the total weight of the composition.

According to yet another embodiment of the invention, the polyelectrolyte may be present in the composition in a content ranging from 0.4% to 15% by weight, in particular from 1% to 10% by weight and especially from 1.5% to 7% by weight relative to the total weight of the composition.

Surfactant

The compositions according to the invention may contain at least one surfactant with an HLB of greater than or equal to 6 at 25° C.

According to one particular embodiment, the compositions may contain a weight content of greater than or equal to 0.1% of surfactant(s) relative to the total weight of the composition. It (they) may especially be present in a proportion ranging from 0.1% to 30%, better still from 1% to 15% and better still from 2% to 10% by weight relative to the total weight of the composition.

It is understood that when the polyelectrolyte is incorporated into the composition of the invention in the form of a composition already formulated with a surfactant with an HLB of greater than or equal to 6 at 25° C., the amount of surfactant defined above takes into account the amount of the said surfactant included in the polyelectrolyte formulation.

The term "HLB of greater than or equal to 6" means a surfactant having at 25° C. an HLB (hydrophilic-lipophilic balance), within the Griffin meaning, of greater than or equal to 6.

The HLB value according to Griffin is defined in J. Soc. Cosm. Chem. 1954 (volume 5), pp 249-256.

Reference may be made to the document "Encyclopedia of Chemical Technology, Kirk-Othmer", volume 22, pp 333-432, 3rd edition, 1979, Wiley, for the definition of the properties and functions (emulsifying) of surfactants, in particular pp 347-377 of this reference, for the nonionic surfactants.

The surfactant with an HLB of greater than or equal to 6 at 25° C. included in the cosmetic composition according to the present invention may be ionic, nonionic or of mixed ionic and nonionic nature.

Cosmetic compositions in which the surfactants with an HLB of greater than or equal to 6 at 25° C. are nonionic are most particularly suitable for use in the present invention.

Among the nonionic surfactants with an HLB of greater than or equal to 6 at 25° C. that may be present in the compositions according to the present invention, used alone or as a mixture, mention may be made especially of:

oxyethylenated and/or oxypropylenated ethers (which may comprise from 1 to 150 oxyethylene and/or oxypropylene groups) of glycerol;

oxyethylenated and/or oxypropylenated ethers (which may comprise from 1 to 150 oxyethylene and/or oxypropylene groups) of fatty alcohols (especially of $C_8$-$C_{24}$ and preferably $C_{12}$-$C_{18}$ alcohol), such as oxyethylenated cetearyl alcohol ether containing 30 oxyethylene groups (CTFA name "Ceteareth-30") and the oxyethylenated ether of the mixture of $C_{12}$-$C_{15}$ fatty alcohols comprising 7 oxyethylene groups (CTFA name "$C_{12-15}$ Pareth-7") sold under the name "Neodol 25-7®" by Shell Chemicals;

fatty acid esters (especially of a $C_8$-$C_{24}$ and preferably $C_{16}$-$C_{22}$ acid) of polyethylene glycol (which may comprise from 1 to 150 ethylene glycol units), such as PEG-50 stearate and PEG-40 monostearate sold under the name Myrj 52P® by the company ICI Uniqema;

fatty acid esters (especially of a $C_8$-$C_{24}$ and preferably $C_{16}$-$C_{22}$ acid) of oxyethylenated and/or oxypropylenated glyceryl ethers (which may comprise from 1 to 150 oxyethylene and/or oxypropylene groups), for instance PEG-200 glyceryl monostearate sold under the name "Simulsol 220 ™®" by the company SEPPIC; glyceryl stearate polyethoxylated with 30 ethylene oxide groups, for instance the product Tagat S® sold by the company Goldschmidt, glyceryl oleate polyethoxylated with 30 ethylene oxide groups, for instance the product Tagat O® sold by the company Goldschmidt, glyceryl cocoate polyethoxylated with 30 ethylene oxide groups, for instance the product Varionic LI 13® sold by the company Sherex, glyceryl isostearate polyethoxylated with 30 ethylene oxide groups, for instance the product Tagat L® sold by the company Goldschmidt, and glyceryl laurate polyethoxylated with 30 ethylene oxide groups, for instance the product Tagat I® from the company Goldschmidt;

fatty acid esters (especially of a $C_8$-$C_{24}$ and preferably $C_{16}$-$C_{22}$ acid) of oxyethylenated and/or oxypropylenated sorbitol ethers (which may comprise from 1 to 150 oxyethylene and/or oxypropylene groups), for instance polysorbate 60 sold under the name "Tween 60®" by the company Uniqema, and also polysorbate 80, polysorbate 40 and polysorbate 20;

dimethicone copolyol, such as the product sold under the name "Q2-5220®" by the company Dow Corning;

dimethicone copolyol benzoate (Finsolv SLB 101® and 201® by the company Finetex);

copolymers of propylene oxide and of ethylene oxide, also known as EO/PO polycondensates;

and mixtures thereof.

The EO/PO polycondensates are more particularly copolymers consisting of polyethylene glycol and polypropylene glycol blocks, for instance polyethylene glycol/polypropylene glycol/polyethylene glycol triblock polycondensates. These triblock polycondensates have, for example, the following chemical structure:

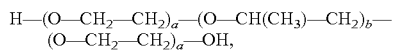

$$H-(O-CH_2-CH_2)_a-(O-CH(CH_3)-CH_2)_b-(O-CH_2-CH_2)_a-OH,$$

in which formula a ranges from 2 to 120 and b ranges from 1 to 100.

The EO/PO polycondensate preferably has a weight-average molecular weight ranging from 1000 to 15,000 and better still ranging from 2000 to 13,000. Advantageously, the said EO/PO polycondensate has a cloud point, at 10 g/l in distilled water, of greater than or equal to 20° C. and preferably greater than or equal to 60° C. The cloud point is measured according to ISO standard 1065. As EO/PO polycondensates that may be used according to the invention, mention may be made of the polyethylene glycol/polypropylene glycol/polyethylene glycol triblock polycondensates sold under the name Synperonic®, for instance Synperonic PE/L44® and Synperonic PE/F127®, by the company ICI.

Among the ionic surfactants, which may be anionic or cationic, with an HLB of greater than or equal to 6 at 25° C., which may be present in the composition according to the present invention, used alone or as a mixture, mention may be made especially of:

silicone surfactants, for instance dimethicone copolyol phosphates such as the product sold under the name Pecosil PS 100® by the company Phoenix Chemical, amino acid derivatives, such as lauryl sarcosinate and lauryl taurate, $C_{16}$-$C_{30}$ fatty acid salts, especially those derived from amines, for instance triethanolamine stearate;

polyoxyethylenated fatty acid salts, especially those derived from amines or alkali metal salts, and mixtures thereof;

phosphoric esters and salts thereof, such as "DEA oleth-10 phosphate" (Crodafos N 10N from the company Croda);

sulfosuccinates such as "Disodium PEG-5 citrate lauryl sulfosuccinate" and "Disodium ricinoleamido MEA sulfosuccinate";

alkyl ether sulfates, such as sodium lauryl ether sulfate;

isethionates;

acylglutamates such as "Disodium hydrogenated tallow glutamate" (Amisoft HS-21 R sold by the company Ajinomoto), and mixtures thereof.

Triethanolamine stearate is most particularly suitable for the invention. This surfactant is generally obtained by simple mixing of stearic acid and triethanolamine.

Representative cationic surfactants that may especially be mentioned include:

alkylimidazolidiniums, such as isostearylethylimidonium ethosulfate, ammonium salts, such as N,N,N-trimethyl-1-docosanaminium chloride (behentrimonium chloride).

The compositions according to the invention may also contain one or more amphoteric surfactants, for instance N-acylamino acids such as N-alkylaminoacetates and disodium cocoamphodiacetate, and amine oxides such as stearamine oxide, or alternatively silicone surfactants, for instance dimethicone polyol phosphates such as the product sold under the name "Pecosil PS 100" by the company Phoenix Chemical.

The nonionic and ionic surfactants with an HLB of greater than or equal to 6 at 25° C. described above may also be present in combination.

Moreover, the cosmetic compositions according to the present invention preferably comprise one or more surfactant(s) with an HLB of greater than or equal to 8 at 25° C., in particular with an HLB of greater than or equal to 10 and especially greater than or equal to 12.

Nonionic surfactants with an HLB of greater than or equal to 6 at 25° C. that are most particularly suitable for use in the invention are oxyethylenated and/or oxypropylenated (possibly comprising from 1 to 150 oxyethylene groups) fatty acid esters of sorbitol ethers, for instance polysorbate 20 with an HLB of 16.7, polysorbate 40 with an HLB of 15.6, polysorbate 60 with an HLB of 14.9 and polysorbate 80 with an HLB of 15.0.

The composition according to the invention may comprise other surfactant(s), which are introduced, for example, into the composition by introduction of the aqueous dispersion of particles of a polymer, these surfactants being those conventionally used to stabilize them.

Aqueous Dispersion of Polymer Particles/Latex and Pseudolatex

Latices and pseudolatices are colloidal dispersions of polymer particles in an aqueous liquid phase. The terms "aqueous dispersion of polymer particles" and "latices and pseudolatices" are used without discrimination in the context of the description of the invention.

The latices are generally obtained by suspension or emulsion polymerization or copolymerization of monomers according to processes that are well known to those skilled in the art. Such monomers may be chosen in particular from styrene, butadiene, acrylonitrile, chloroprene, vinyl acetate, urethanes, isoprene, isobutylene, and acrylic or methacrylic acid, maleic acid, crotonic acid or itaconic acid or esters or amides thereof.

The term "pseudolatex" denotes a dispersion consisting of generally spherical particles of a polymer, these particles being obtained by dispersing the polymer in a suitable aqueous phase.

The term "pseudolatex" should not be confused with the terms "latex" and "synthetic latex" which also mean a dispersion consisting of particles of a polymer that are obtained directly by polymerization of one or more monomers in a suitable aqueous phase as mentioned above.

These latices or pseudolatices have film-forming properties that are advantageous for imparting water resistance to the cosmetic compositions that are the subjects of the invention. The polymers included in these latices or pseudolatices are thus also referred to as film-forming polymers.

More specifically, in the present invention, the term "film-forming polymer" means a polymer capable of forming, by itself or in the presence of an auxiliary film-forming agent, a macroscopically continuous film that adheres to the keratin materials, and preferably a cohesive film, and better still a film whose cohesion and mechanical properties are such that the said film can be isolated and manipulated in isolation, for example when the said film is prepared by casting on a non-stick surface, for instance a Teflon-coated or silicone-coated surface.

Among the film-forming polymers that may be included in the latex or pseudolatex included in the composition according to the present invention, mention may be made of synthetic polymers of the polycondensate type or of the free-radical type.

These film-forming polymers are preferably different from the polyelectrolyte defined previously.

Synthetic Polymers

Among the polycondensates, mention may also be made of anionic, cationic, nonionic or amphoteric polyurethanes, polyurethane-acrylics, polyurethane-polyvinyl-pyrrolidones, polyester-polyurethanes, polyether-polyurethanes, polyureas, polyurea/poly-urethanes, and mixtures thereof.

The polyurethanes may be, for example, an aliphatic, cycloaliphatic or aromatic polyurethane, polyurea/polyurethane or polyurea copolymer, containing, alone or as a mixture:

at least one block of linear or branched aliphatic and/or cycloaliphatic and/or aromatic polyester origin, and/or at least one block of aliphatic and/or cycloaliphatic and/or aromatic polyether origin, and/or at least one substituted or unsubstituted, branched or unbranched silicone block, for example polydimethylsiloxane or polymethylphenylsiloxane, and/or at least one block comprising fluoro groups.

The polyurethanes as defined in the invention may also be obtained from branched or unbranched polyesters or from alkyds containing labile hydrogens, which are modified by means of a polyaddition with a diisocyanate and a difunctional organic co-reactive compound (for example dihydro, diamino or hydroxyamino), also containing either a carboxylic acid or carboxylate group, or a sulfonic acid or sulfonate group, or alternatively a neutralizable tertiary amine group or a quaternary ammonium group.

Mention may also be made of polyesters, polyesteramides, fatty-chain polyesters, polyamides and epoxyester resins.

The polyesters may be obtained, in a known manner, by polycondensation of aliphatic or aromatic diacids with aliphatic or aromatic diols or with polyols. Succinic acid, glutaric acid, adipic acid, pimelic acid, suberic acid or sebacic acid may be used as aliphatic diacids. Terephthalic acid or isophthalic acid, or alternatively a derivative such as phthalic anhydride, may be used as aromatic diacids. Ethylene glycol, propylene glycol, diethylene glycol, neopentyl glycol, cyclohexanedimethanol and 4,4-N-(1-methylpropylidene)bisphenol may be used as aliphatic diols. Glycerol, pentaerythritol, sorbitol and trimethylolpropane may be used as polyols.

The polyesteramides may be obtained in a similar manner to the polyesters, by polycondensation of diacids with diamines or amino alcohols. Ethylenediamine, hexa-methylenediamine or meta- or para-phenylenediamine may be used as diamine. Monoethanolamine may be used as amino alcohol.

As monomer bearing an anionic group that may be used during the polycondensation, mention may be made, for example, of dimethylolpropionic acid, trimellitic acid or a derivative such as trimellitic anhydride, the sodium salt of pentanediol-3-sulfonic acid and the sodium salt of 5-sulfo-1, 3-benzenedicarboxylic acid. The fatty-chain polyesters may be obtained using fatty-chain diols during the polycondensation. The epoxy ester resins may be obtained by polycondensation of fatty acids with a condensate having $\alpha,\omega$-diepoxy ends.

The free-radical polymers may in particular be acrylic and/or vinyl polymers or copolymers.

The acrylic polymers may result from the copolymerization of monomers chosen from the esters and/or amides of acrylic acid or of methacrylic acid. As examples of monomers of ester type, mention may be made of methyl methacrylate, ethyl methacrylate, butyl methacrylate, isobutyl methacrylate, 2-ethylhexyl methacrylate and lauryl methacrylate. As examples of monomers of amide type, mention may be made of N-t-butylacrylamide and N-t-octylacrylamide.

Acrylic polymers obtained by copolymerization of ethylenically unsaturated monomers containing hydrophilic groups, preferably of nonionic nature, such as hydroxyethyl acrylate, 2-hydroxypropyl acrylate, hydroxyethyl methacrylate and 2-hydroxypropyl methacrylate, are preferably used.

The vinyl polymers may result from the homopolymerization or copolymerization of monomers chosen from vinyl esters, styrene or butadiene. As examples of vinyl esters, mention may be made of vinyl acetate, vinyl neodecanoate, vinyl pivalate, vinyl benzoate and vinyl t-butylbenzoate.

Acrylic/silicone copolymers or nitrocellulose/acrylic copolymers may also be used.

Mention may also be made of the polymers resulting from the free-radical polymerization of one or more free-radical monomers inside and/or partially at the surface of preexisting particles of at least one polymer chosen from the group consisting of polyurethanes, polyureas, polyesters, polyesteramides and/or alkyds. These polymers are generally referred to as "hybrid polymers".

Aqueous dispersions of film-forming polymers that may be used include the acrylic dispersions sold under the names "Neocryl XK-90®", "Neocryl A1070®", "Neocryl A-1090®", "Neocryl BT-62®", "Neocryl A-1079®" and "Neocryl A-523®" by the company Avecia-Neoresins, "Dow Latex 432®" by the company Dow Chemical, "Daitosol 5000 AD®" or "Daitosol 5000 SJ®" by the company Daito Kasey Kogyo; "Syntran 5760®" by the company Interpolymer, "Allianz Opt®" by the company Rohm & Haas, or the aqueous dispersions of polyurethane sold under the names "Neorez R-981®" and "Neorez R-974®" by the company Avecia-Neoresins, "Avalure UR-405®", "Avalure UR-410®", "Avalure UR-425®", "Avalure UR-450®", "Sancure 875®", "Sancure 861®", "Sancure 878®" and "Sancure 2060®" by the company Goodrich, "Impranil 85®" by the company Bayer and "Aquamere H-1511®" by the company Hydromer; the sulfopolyesters sold under the brand name "Eastman AQ®" by the company Eastman Chemical Products, vinyl dispersions, for instance "Mexomer PAM", aqueous dispersions of polyvinyl acetate, for instance "Vinybran®" from the company Nisshin Chemical, or those sold by the company Union Carbide, aqueous dispersions of terpolymer of vinylpyrrolidone, dimethylaminopropylmethacrylamide and lauryldimethylpropylmethacrylamidoammonium chloride, such as "Styleze W" from ISP, aqueous dispersions of polyurethane/polyacrylic hybrid polymers, such as those sold under the references "Hybridur®" by the company Air Products or "Duromer®" from National Starch, dispersions of core/shell type: for example those sold by the company Atofma under the reference "Kynar" (core: fluoro-shell: acrylic) or those described in document U.S. Pat. No. 5,188, 899 (core: silica-shell: silicone), and mixtures thereof.

The solids content of the aqueous dispersion of particles of a polymer is greater than or equal to 2%, especially greater than or equal to 5%, in particular greater than or equal to 7% and in particular to 10%, and especially less than 50% and more particularly than 30%, by weight relative to the total weight of the composition.

According to certain embodiments of the invention, the polymer constituting the particles of the aqueous dispersion is different from a copolymer obtained by condensation of diethylene glycol, cyclohexanedimethanol, isophthalic acid and sulfoisophthalic acid. This particular copolymer obtained by condensation of diethylene glycol, cyclohexanedimethanol, isophthalic acid and sulfoisophthalic acid is included in the category of sulfopolyesters. It is sold especially under the brand name "Eastman AQ®" by the company Eastman Chemical Products, for example under the references "Eastman AQ 55-S®" or "Eastman AQ 38-S®".

It is possible for the polymer constituting the particles of the aqueous dispersion not to comprise an ionizable monomer. The sulfopolyesters mentioned above especially comprise such ionizable monomers, which gives them a certain affinity for water. However, compositions in which the film-forming polymers do not have such an affinity for water are preferred.

According to one embodiment of the invention, the composition may comprise a plasticizer that promotes the formation of a film with the film-forming polymer. Such a plasticizer may be chosen from any compound known to those skilled in the art as being capable of fulfilling the desired function.

Water and/or Water-Soluble Solvent

The compositions according to the invention comprise an aqueous phase comprising water and/or at least one water-soluble solvent.

In the present invention, the term "water-soluble solvent" denotes a compound that is liquid at room temperature and water-miscible (miscibility in water of greater than 50% by weight at 25° C. and atmospheric pressure).

The water-soluble solvents that may be used in the compositions according to the invention may also be volatile.

Among the water-soluble solvents that may be used in the compositions according to the invention, mention may be made especially of lower monoalcohols containing from 1 to 5 carbon atoms, such as ethanol and isopropanol, glycols containing from 2 to 8 carbon atoms, such as ethylene glycol, propylene glycol, 1,3-butylene glycol and dipropylene glycol, $C_3$ and $C_4$ ketones and $C_2$-$C_4$ aldehydes.

The aqueous phase (water and/or water-soluble solvent(s)) may be introduced in unmodified form into the formulation according to the invention or may be incorporated therein by means of one or more ingredients constituting the said composition. Thus, water may especially be introduced into the composition by means of introducing the latex or pseudolatex.

The content of water and/or of water-soluble solvent(s) in the compositions according to the invention is preferably between 20% and 90%, more preferably between 25% and 70% and more particularly between 30% and 65% by weight relative to the total weight of the composition.

The cosmetic compositions may also comprise a dissolved salt. This salt may be any cosmetically acceptable mineral or organic salt. In this respect, mention may be made especially of EDTA, sodium dehydroacetate, NaCl, KCl, $CuSO_4$, $MgCl_2$, NaOH and $Na_2SO_4$. Preferably, this salt has a molar mass of less than or equal to 5000 g/mol and especially 800 g/mol. The salt within the meaning of the present invention is preferably different from the surfactant as defined above.

According to one particularly preferred variant of the invention, the latex or pseudolatex may be present in a content of greater than or equal to 5% by weight, and more particularly of greater than or equal to 10% by weight relative to the total weight of the composition, in which case the composition comprises at least one salt.

Structuring Agent

The compositions according to the invention may comprise at least one agent for structuring the oily phase or organic solvent, chosen from waxes, semi-crystalline polymers and lipophilic gelling agents, and mixtures thereof. In embodiments, the structuring agent is chosen from waxes and semi-crystalline polymers.

The structuring agent may represent from 0.1% to 80% by weight, preferably from 0.5% to 50% and even more preferably from 1% to 40% by weight relative to the total weight of the composition. The amount of oily structuring agent may be adjusted by a person skilled in the art as a function of the structuring properties of the said agents.

Wax(es)

The wax is generally a lipophilic compound that is solid at room temperature (25° C.), with a solid/liquid reversible change of state, having a melting point of greater than or equal to 30° C., which may be up to 200° C. and in particular up to 120° C.

By bringing the wax to the liquid form (melting), it is possible to make it miscible with oils and to form a microscopically uniform mixture, but on cooling the mixture to room temperature, recrystallization of the wax in the oils of the mixture is obtained.

In particular, the waxes that are suitable for the invention may have a melting point of greater than or equal to 45° C. and in particular greater than or equal to 55° C.

For the purposes of the invention, the melting point corresponds to the temperature of the most endothermic peak observed by thermal analysis (DSC) as described in ISO standard 11357-3; 1999. The melting point of the wax may be measured using a differential scanning calorimeter (DSC), for example the calorimeter sold under the name "MDSC 2920" by the company TA Instruments.

The measuring protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature increase ranging from −20° C. to 100° C. at a heating rate of 5° C./minute. During the second temperature increase, the variation of the difference in power absorbed by the empty crucible and by the crucible containing the sample of wax is measured as a function of the temperature. The melting point of the compound is the temperature value corresponding to the top of the peak of the curve representing the variation in the difference in absorbed power as a function of the temperature.

The waxes that may be used in the compositions according to the invention are chosen from waxes that are solid at room temperature of animal, plant, mineral or synthetic origin, and mixtures thereof.

The waxes that may be used in the compositions according to the invention generally have a hardness ranging from 0.01 MPa to 15 MPa, especially greater than 0.05 MPa and in particular greater than 0.1 MPa.

The hardness is determined by measuring the compression force, measured at 20° C. using a texturometer sold under the name TA-XT2i® by the company Rheo, equipped with a stainless-steel cylindrical spindle 2 mm in diameter, by measuring the change in force (compression force or stretching force) (F) as a function of time, during the following operation:

The spindle is displaced at a speed of 0.1 mm/s and then penetrates the wax to a penetration depth of 0.3 mm. When the spindle has penetrated the wax to a depth of 0.3 mm, the spindle is held still for 1 second (corresponding to the relaxation time) and is then withdrawn at a speed of 0.1 mm/s. During the relaxation time, the force (compression force) decreases greatly until it becomes zero, and then, during the withdrawal of the spindle, the force (stretching force) becomes negative and then rises again towards the value 0. The hardness corresponds to the maximum compression force measured between the surface of the spindle and the wax at the moment they come into contact. The value of this force is expressed in MPa.

To measure the hardness, the wax is melted at a temperature equal to the melting point of the wax+20° C. The molten wax is poured into a container 30 mm in diameter and 20 mm deep. The wax is recrystallized at room temperature (25° C.)

for 24 hours and is then stored for at least 1 hour at 20° C., before performing the hardness measurement.

As illustrations of waxes that are suitable for the invention, mention may be made especially of hydrocarbon-based waxes, for instance beeswax, lanolin wax, Chinese insect waxes, sumach wax, paraffins, certain polyethylene waxes and waxy copolymers, and also esters thereof.

Mention may also be made of waxes obtained by catalytic hydrogenation of animal or plant oils containing linear or branched $C_8$-$C_{32}$ fatty chains. Among these waxes that may especially be mentioned are isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane) tetrastearate sold under the name Hest 2T-4S® by the company Heterene.

Mention may also be made of silicone waxes and fluoro waxes.

The waxes obtained by hydrogenation of castor oil esterified with cetyl alcohol, sold under the names Phytowax ricin 16L64® and 22L73® by the company Sophim may also be used. Such waxes are described in patent application FR-A-2 792 190.

According to one particular embodiment, the compositions according to the invention may comprise at least one "tacky" wax, i.e. a wax with a tack of greater than or equal to 0.7 N.s and a hardness of less than or equal to 3.5 MPa.

The use of a tacky wax may especially allow the production of a cosmetic composition that applies easily to keratin fibres, with good attachment to the keratin fibres, and which leads to the formation of a smooth, homogeneous and thickening makeup.

The tacky wax used may especially have a tack ranging from 0.7 N.s to 30 N.s, in particular greater than or equal to 1 N.s, especially ranging from 1 N.s to 20 N.s, in particular greater than or equal to 2 N.s, especially ranging from 2 N.s to 10 N.s and in particular ranging from 2 N.s to 5 N.s.

The tack of the wax is determined by measuring the change in force (compression force or stretching force) as a function of time, at 20° C., using the texturometer sold under the name TA-TX2i® by the company Rheo, equipped with a conical acrylic polymer spindle forming an angle of 45°.

The measuring protocol is as follows:

The wax is melted at a temperature equal to the melting point of the wax+10° C. The molten wax is poured into a container 25 mm in diameter and 20 mm deep. The wax is recrystallized at room temperature (25° C.) for 24 hours such that the surface of the wax is flat and smooth, and the wax is then stored for at least 1 hour at 20° C. before measuring the tack.

The texturometer spindle is displaced at a speed of 0.5 mm/s then penetrates the wax to a penetration depth of 2 mm. When the spindle has penetrated the wax to a depth of 2 mm, the spindle is held still for 1 second (corresponding to the relaxation time) and is then withdrawn at a speed of 0.5 mm/s.

During the relaxation time, the force (compression force) decreases greatly until it becomes zero, and then, during the withdrawal of the spindle, the force (stretching force) becomes negative and then rises again to the value 0. The tack corresponds to the integral of the curve of the force as a function of time for the part of the curve corresponding to negative values of the force (stretching force). The tack value is expressed in N.s.

The tacky wax that may be used generally has a hardness of less than or equal to 3.5 MPa, in particular ranging from 0.01 MPa to 3.5 MPa, especially ranging from 0.05 MPa to 3 MPa or even ranging from 0.1 MPa to 2.5 MPa.

The hardness is measured according to the protocol described previously.

Tacky waxes that may be used include a $C_{20}$-$C_{40}$ alkyl (hydroxystearyloxy)-stearate (the alkyl group containing from 20 to 40 carbon atoms), alone or as a mixture, in particular a $C_{20}$-$C_{40}$ alkyl 12-(12'-hydroxystearyloxy)stearate, of formula (I):

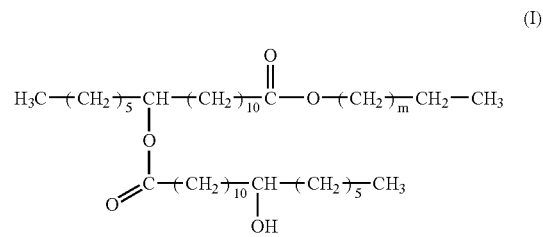

in which m is an integer ranging from 18 to 38, or a mixture of compounds of formula (I).

Such a wax is especially sold under the names Kester Wax K 82 P® and Kester Wax K 80 P® by the company Koster Keunen.

The waxes mentioned above generally have a starting melting point of less than 45° C.

In the present invention, waxes provided in the form of small particles having a dimension expressed as the mean "effective" volume diameter D [4.3] of about from 0.5 to 30 micrometers, in particular from 1 to 20 micrometers and more particularly from 5 to 10 micrometers, which are referred to hereinafter as "microwaxes", may also be used. For the purpose of distinction, the waxes used according to the invention in the form of fragments of larger size are referred to hereinbelow as "conventional waxes".

The particle sizes may be measured by various techniques; mention may be made in particular of light-scattering techniques (dynamic and static), Coulter counter methods, sedimentation rate measurements (related to the size via Stokes' law) and microscopy. These techniques make it possible to measure a particle diameter and, for some of them, a particle size distribution.

The sizes and size distributions of the particles in the compositions according to the invention are preferably measured by static light scattering using a commercial granulometer such as the MasterSizer 2000 from Malvern. The data are processed on the basis of the Mie scattering theory. This theory, which is exact for isotropic particles, makes it possible to determine an "effective" particle diameter in the case of non-spherical particles. This theory is described especially in the publication by Van de Hulst, H. C., "Light Scattering by Small Particles," Chapters 9 and 10, Wiley, New York, 1957.

As microwaxes that may be used in the compositions according to the invention, mention may in particular be made of carnauba microwaxes, such as the product sold under the name "MicroCare 350®" by the company Micro Powders, synthetic microwaxes, such as the product sold under the name "MicroEase 114S®" by the company Micro Powders, microwaxes consisting of a mixture of carnauba wax and polyethylene wax, such as the products sold under the names "Micro Care 300®" and "Micro Care 310®" by the company Micro Powders, microwaxes consisting of a mixture of carnauba wax and of synthetic wax, such as the product sold under the name "Micro Care 325®" by the company Micro Powders, polyethylene microwaxes, such as the products sold under the names "Micropoly 200®", "Micropoly 220®", "Micropoly 220L®" and "Micropoly 250S®" by the company Micro Powders, and polytetrafluoroethylene micropowders such as the products sold under the names "Microslip 519®" and "Microslip 519 L®" by the company Micro Powders.

In the compositions according to the invention, it is obviously possible to use a mixture of waxes and especially to use one or more conventional waxes, such as, especially, a tacky wax and/or a wax with a starting melting point of greater than or equal to 45° C., and one or more waxes known as microwaxes. The composition according to the invention may comprise a content of waxes ranging from 0 to 70% by weight relative to the total weight of the composition; it may in particular contain from 0.5% to 50% and more particularly from 1% to 30% thereof.

Semi-Crystalline Polymers

The term "polymer" means compounds containing at least two repeating units, preferably at least three repeating units and more especially at least ten repeating units. The term "semi-crystalline polymer" means polymers comprising a crystallizable portion, a crystallizable side chain or a crystallizable block in the skeleton, and an amorphous portion in the skeleton and having a first-order reversible phase-change temperature, in particular of melting (solid-liquid transition). When the crystallizable portion is in the form of a crystallizable block of the polymer skeleton, the amorphous portion of the polymer is in the form of an amorphous block; in this case, the semi-crystalline polymer is a block copolymer, for example, of the diblock, triblock or multiblock type, comprising at least one crystallizable block and at least one amorphous block. The term "block" generally means at least five identical repeating units. The crystallizable block(s) is (are) of chemical nature different from that of the amorphous block(s).

The semi-crystalline polymer has a melting point of greater than or equal to 30° C. (especially ranging from 30° C. to 80° C.), preferably ranging from 30° C. to 60° C. This melting point is a first-order change of state temperature.

This melting point may be measured by any known method and in particular using a differential scanning calorimeter (DSC).

Advantageously, the semi-crystalline polymer(s) has (have) a number-average molecular mass of greater than or equal to 1000 and especially a number-average molecular mass Mn ranging from 2000 to 800,000, preferably from 3000 to 500,000, better still from 4000 to 150,000, especially less than 100,000 and better still from 4000 to 99,000. For the purposes of the invention, the term "crystallizable chain or block" means a chain or block which, if it were alone, would reversibly change from the amorphous state to the crystalline state, depending on whether the system is above or below the melting point. For the purposes of the invention, a chain is a group of atoms, which is pendent or lateral relative to the polymer skeleton. A block is a group of atoms belonging to the skeleton, this group constituting one of the repeating units of the polymer. Advantageously, the "crystallizable side chain" may be a chain containing at least six carbon atoms.

The semi-crystalline polymer may be chosen from block copolymers comprising at least one crystallizable block and at least one amorphous block, and homopolymers and copolymers bearing at least one crystallizable side chain per repeating unit, and mixtures thereof.

Such polymers are described, for example, in document EP 1 396 259.

A. Semi-Crystalline Polymers Containing Crystallizable Side Chains

Mention may be made in particular of those defined in U.S. Pat. No. 5,156,911. They are homopolymers or copolymers comprising from 50% to 100% by weight of units resulting from the polymerization of one or more monomers bearing a crystallizable hydrophobic side chain.

These homopolymers or copolymers are of any nature, provided that they meet the conditions mentioned previously.

B. Polymers Bearing in the Skeleton at Least One Crystallizable Block

These polymers are especially block copolymers containing at least two blocks of different chemical nature, one of which is crystallizable.

The block polymers defined in U.S. Pat. No. 5,156,911 may be used;

The block copolymers of olefin or of cycloolefin containing a crystallizable chain, for instance those derived from the block polymerization of:

cyclobutene, cyclohexene, cyclooctene, norbornene (i.e. bicyclo(2,2,1)-2-heptene), 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-octahydronaphthalene, dicyclopentadiene, or mixtures thereof, with ethylene, propylene, 1-butene, 3-methyl-1-butene, 1-hexene, 4-methyl-1-pentene, 1-octene, 1-decene or 1-eicosene, or mixtures thereof, and in particular copoly(ethylene/norbornene) blocks and (ethylene/propylene/ethylidene-norbornene) block terpolymers. Those resulting from the block copolymerization of at least 2 $C_2$-$C_{16}$, better still $C_2$-$C_{12}$ and even better still $C_4$-$C_{12}$α-olefins such as those mentioned above and in particular block bipolymers of ethylene and of 1-octene may also be used.

The copolymers may be copolymers containing at least one crystallizable block, the rest of the copolymer being amorphous (at room temperature). These copolymers may also contain two crystallizable blocks of different chemical nature. The preferred copolymers are those that simultaneously contain at room temperature a crystallizable block and an amorphous block that are both hydrophobic and lipophilic, sequentially distributed; mention may be made, for example, of polymers containing one of the crystallizable blocks and one of the amorphous blocks below:

Block that is crystallizable by nature: a) of polyester type, for instance poly(alkylene terephthalate), b) of polyolefin type, for instance polyethylenes or polypropylenes.

Amorphous and lipophilic block, for instance: amorphous polyolefins or copoly(olefin)s such as poly(isobutylene), hydrogenated polybutadiene or hydrogenated poly(isoprene).

As examples of such copolymers containing a crystallizable block and an amorphous block which are different, mention may be made of:

α) poly(ε-caprolactone)-b-poly(butadiene) block copolymers, preferably used hydrogenated, such as those described in the article "Melting behavior of poly(ε-caprolactone)-block-polybutadiene copolymers" from S. Nojima, Macromolecules, 32, 3727-3734 (1999), β) the hydrogenated block or multiblock poly(butylene terephthalate)-b-poly(isoprene) block copolymers cited in the article "Study of morphological and mechanical properties of PP/PBT" by B. Boutevin et al., Polymer Bulletin, 34, 117-123 (1995), γ) the poly(ethylene)-b-copoly(ethylene/propylene) block copolymers cited in the articles "Morphology of semi-crystalline block copolymers of ethylene-(ethylene-alt-propylene)" by P. Rangarajan et al., Macromolecules, 26, 4640-4645 (1993) and "Polymer aggregates with crystalline cores: the system poly(ethylene)-poly(ethylene-propylene)" by P. Richter et al., Macromolecules, 30, 1053-1068 (1997), δ) the poly(ethylene)-b-poly(ethylethylene) block copolymers cited in the general article D10 "Crystallization in block copolymers" by I. W. Hamley, Advances in Polymer Science, Vol. 148, 113-137 (1999).

Preferably, the semi-crystalline polymers suitable for the compositions according to the invention are non-crosslinked.

This polymer may be chosen in particular from copolymers resulting from the polymerization of at least one monomer containing a crystallizable chain chosen from saturated $C_{14}$-$C_{24}$ alkyl (meth)acrylates, $C_{11}$-$C_{15}$ perfluoroalkyl (meth)acrylates, $C_{14}$ to $C_{24}$ N-alkyl(meth)acrylamides with or without a fluorine atom, vinyl esters containing $C_{14}$ to $C_{24}$ alkyl or perfluoroalkyl chains, vinyl ethers containing $C_{14}$ to $C_{24}$ alkyl or perfluoroalkyl chains, $C_{14}$ to $C_{24}$ α-olefins, para-alkylstyrenes with an alkyl group containing from 12 to 24 carbon atoms, with at least one optionally fluorinated $C_1$ to $C_{10}$ monocarboxylic acid ester or amide, which may be represented by the following formula:

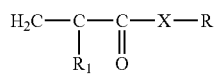

in which $R_1$ is H or $CH_3$, R represents an optionally fluorinated $C_1$-$C_{10}$ alkyl group and X represents O, NH or $NR_2$, in which $R_2$ represents an optionally fluorinated $C_1$-$C_{10}$ alkyl group.

According to a more particular embodiment of the invention, the polymer is derived from a monomer containing a crystallizable chain chosen from saturated $C_{14}$-$C_{22}$ alkyl (meth)acrylates.

As a particular example of a structuring semi-crystalline polymer that may be used in the compositions according to the invention, mention may be made of the Intelimer® products from the company Landec described in the brochure "Intelimer® polymers", Landec IP22 (Rev. 4-97). These polymers are in solid form at room temperature (25° C.). They bear crystallizable side chains and have the above formula X.

Oils

The compositions according to the invention may comprise at least one organic oil or solvent. This may be a mixture of organic oils or solvents.

The compositions according to the invention may comprise a total amount of oil ranging from 1% to 30%, especially from 8% to 25% and in particular from 10% to 20% by weight relative to the total weight of the composition, which may also be referred to as a non-aqueous solvent medium.

The oil(s) present in the composition of the invention may be chosen from volatile oils and/or non-volatile oils, and mixtures thereof.

Cosmetic compositions essentially comprising volatile oils prove to be most particularly advantageous in the context of the present invention.

The term "volatile organic oil or solvent" means an organic oil or solvent (or non-aqueous medium) capable of evaporating on contact with the skin in less than one hour, at room temperature and atmospheric pressure.

The volatile oil is a volatile cosmetic oil, which is liquid at room temperature, especially having a non-zero vapour pressure, at room temperature and atmospheric pressure, in particular having a vapour pressure ranging from 0.13 Pa to 40,000 Pa ($10^{-3}$ to 300 mmHg) and preferably ranging from 1.3 Pa to 8000 Pa (0.01 to 60 mmHg).

The volatile oils (or organic solvents) may be hydrocarbon-based oils, silicone oils or fluoro oils, or mixtures thereof.

The term "hydrocarbon-based oil" means an oil mainly containing hydrogen and carbon atoms and possibly oxygen, nitrogen, sulfur and/or phosphorus atoms. The volatile hydrocarbon-based oils may be chosen from hydrocarbon-based oils containing from 8 to 16 carbon atoms, and especially branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane, isohexadecane, and for example the oils sold under the trade names "Isopar®" or Permethyl®, branched $C_8$-$C_{16}$ esters, isohexyl neopentanoate, and mixtures thereof. Other volatile hydrocarbon-based oils, for instance petroleum distillates, especially those sold under the name "Shell Solt®" by the company Shell, may also be used.

Volatile oils that may also be used include volatile silicones, for instance volatile linear or cyclic silicone oils, especially those with a viscosity 6 centistokes ($6 \times 10^{-6}$ m$^2$/s) and especially containing from 3 to 6 silicon atoms, these silicones optionally comprising one or more alkyl or alkoxy groups containing 1 or 2 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, heptamethylethyltrisiloxane and heptamethylbutyltrisiloxane, and mixtures thereof.

Volatile organic solvents, especially fluorinated solvents such as nonafluoro-methoxybutane or perfluoromethylcyclopentane, may also be used.

Advantageously, the volatile oil(s) is or are chosen from hydrocarbon-based volatile oils containing from 8 to 16 carbon atoms, such as isododecane, volatile silicone oils such as decamethylcyclopentasiloxane (D5) or dodecamethylcyclohexasiloxane (D6), and mixtures thereof.

The compositions according to the invention may also comprise at least one non-volatile compound, which is water-insoluble and liquid at room temperature, especially at least one non-volatile organic solvent or oil, which may be chosen in particular from non-volatile hydrocarbon-based oils and/or silicone oils and/or fluoro oils.

Non-volatile hydrocarbon-based oils that may especially be mentioned include:

hydrocarbon-based oils of plant origin, such as triglycerides consisting of fatty acid esters of glycerol, the fatty acids of which may have varied chain lengths from $C_4$ to $C_{24}$, these chains possibly being linear or branched, and saturated or unsaturated; these oils are especially wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, sesame seed oil, marrow oil, rapeseed oil, blackcurrant oil, evening primrose oil, millet oil, barley oil, quinoa oil, rye oil, safflower oil, candlenut oil, passionflower oil or musk rose oil; or caprylic/capric acid triglycerides, for instance those sold by the company Stéarineries Dubois or those sold under the names Miglyol 810®, 812® and 818® by the company Dynamit Nobel, synthetic ethers containing from 10 to 40 carbon atoms, linear or branched hydrocarbons of mineral or synthetic origin, such as petroleum jelly, polydecenes, hydrogenated polyisobutene such as parleam, and squalane, and mixtures thereof, synthetic esters, for instance oils of formula $R_1COOR_2$ in which $R_1$ represents a linear or branched fatty acid residue containing from 1 to 40 carbon atoms and $R_2$ represents a hydrocarbon-based chain, which is especially branched, containing from 1 to 40 carbon atoms, on condition that $R_1+R_2 \geq 10$, for instance purcellin oil (cetostearyl octanoate), isopropyl myristate, isopropyl palmitate, $C_{12}$ to $C_{15}$ alkyl benzoate, hexyl laurate, diisopropyl adipate, isononyl isononanoate, 2-ethylhexyl palmitate, isostearyl isostearate, alcohol or polyalcohol octanoates, decanoates or ricinoleates, for instance propylene glycol dioctanoate; hydroxylated esters, for instance isostearyl lactate or diisostearyl malate; and pentaerythritol esters, fatty alcohols that are liquid at room temperature with a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol, higher fatty acids such as oleic acid, linoleic acid or linolenic acid, and mixtures thereof.

The non-volatile silicone oils that may be used in the composition according to the invention may be non-volatile polydimethylsiloxanes (PDMS), polydimethylsiloxanes comprising alkyl or alkoxy groups, which are pendent and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyltrimethylsiloxysilicates.

The fluoro oils that may be used in the composition of the invention are especially fluorosilicone oils, fluoro polyethers or fluoro silicones as described in document EP-A-847 752.

The content of non-volatile organic solvent or oil in the compositions according to the invention may range from 0.01% to 30% by weight, in particular from 0.1% to 25% by weight and better still from 0.1% to 20% relative to the total weight of the composition.

Additives

Needless to say, a person skilled in the art will take care to select the optional additional additives and/or the amount thereof such that the advantageous properties of the composition according to the invention are not, or are not substantially, adversely affected by the envisaged addition.

Additional Film-Forming Polymer

The compositions according to the invention may comprise, besides the film-forming polymer dispersed in the aqueous phase in the form of particles, required according to the invention, at least one additional film-forming polymer.

The additional film-forming polymer may be present in the composition according to the invention in a solids content ranging from 0.1% to 60% by weight, preferably from 0.5% to 40% by weight and better still from 1% to 30% by weight relative to the total weight of the composition.

Among the film-forming polymers that may be used in the composition of the present invention, mention may be made of the water-soluble or liposoluble polymers or the polymers in non-aqueous dispersion, detailed below.

Dyestuff

The compositions according to the invention may also comprise at least one dyestuff, for instance pulverulent dyes, liposoluble dyes and water-soluble dyes.

The pulverulent dyestuffs may be chosen from pigments and nacres.

The pigments may be white or coloured, mineral and/or organic, and coated or uncoated. Among the mineral pigments that may be mentioned are titanium dioxide, optionally surface-treated, zirconium oxide, zinc oxide or cerium oxide, and also iron oxide or chromium oxide, manganese violet, ultramarine blue, chromium hydrate and ferric blue. Among the organic pigments that may be mentioned are carbon black, pigments of D & C type, and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica with, especially, ferric blue or chromium oxide, titanium mica with an organic pigment of the abovementioned type, and also nacreous pigments based on bismuth oxychloride.

The liposoluble dyes are, for example, Sudan red, D&C Red 17, D&C Green 6,β-carotene, soybean oil, Sudan brown, D&C Yellow 11, D&C Violet 2, D&C Orange 5, quinoline yellow and annatto.

These dyestuffs may be present in a content ranging from 0.01% to 30% by weight relative to the total weight of the composition.

Fillers

The compositions according to the invention may also comprise at least one filler.

The fillers may be chosen from those that are well known to persons skilled in the art and commonly used in cosmetic compositions. The fillers may be mineral or organic, and lamellar or spherical. Mention may be made of talc, mica, silica, kaolin, polyamide powders, for instance the Nylon® sold under the trade name Orgasol® by the company Atochem, poly-β'-alanine powders and polyethylene powders, powders of tetra-fluoroethylene polymers, for instance Teflon®, lauroyllysine, starch, boron nitride, expanded polymeric hollow microspheres such as those of polyvinylidene chloride/acrylonitrile, for instance the products sold under the name Expancel® by the company Nobel Industrie, acrylic powders, such as those sold under the name Polytrap® by the company Dow Corning, polymethyl methacrylate particles and silicone resin microbeads (for example Tospearls® from Toshiba), precipitated calcium carbonate, magnesium carbonate and magnesium hydrocarbonate, hydroxyapatite, hollow silica microspheres (Silica Beads® from Maprecos), glass or ceramic microcapsules, metal soaps derived from organic carboxylic acids containing from 8 to 22 carbon atoms and in particular from 12 to 18 carbon atoms, for example zinc, magnesium or lithium stearate, zinc laurate and magnesium myristate, and heat-expandable particles such as non-expanded microspheres of copolymer of vinylidene chloride/acrylonitrile/methyl methacrylate or of acrylonitrile homopolymer copolymer, for instance those sold, respectively, under the references Expancel® 820 DU 40 and Expancel® 007WU by the company Akzo Nobel.

The fillers may represent from 0.1% to 25% and in particular from 1% to 20% by weight relative to the total weight of the composition.

Fibres

The compositions according to the invention may also comprise fibres that especially allow an improvement in the lengthening effect when the composition is a mascara.

The term "fibre" should be understood as meaning an object of length L and diameter D such that L is very much greater than D, D being the diameter of the circle in which the cross section of the fibre is inscribed. In particular, the ratio L/D (or shape factor) is chosen in the range from 3.5 to 2500, especially from 5 to 500 and more particularly from 5 to 150.

The fibres that may be used in the compositions of the invention may be mineral or organic fibres of synthetic or natural origin. They may be short or long, individual or organized, for example braided, and hollow or solid. They may have any shape, and may especially have a circular or polygonal (square, hexagonal or octagonal) cross section, depending on the intended specific application. In particular, their ends are blunt and/or polished to prevent injury.

In particular, the fibres have a length ranging from 1 µm to 10 mm, preferably from 0.1 mm to 5 mm and better still from 0.3 mm to 3.5 mm. Their cross section may be within a circle of diameter ranging from 2 nm to 500 µm, particularly ranging from 100 nm to 100 µm and more particularly from 1 µm to 50 µM. The weight or yarn count of the fibres is often given in denier or decitex, and represents the weight in grams per 9 km of yarn. In particular, the fibres may have a yarn count chosen in the range from 0.15 to 30 denier and better still from 0.18 to 18 denier.

The fibres that may be used in the compositions of the invention may be chosen from rigid or non-rigid fibres, and may be of synthetic or natural, mineral or organic origin.

Moreover, the fibres may or may not be surface-treated, may be coated or uncoated, and may be coloured or uncoloured.

As fibres that may be used in the compositions according to the invention, mention may be made of non-rigid fibres such as polyamide (Nylon®) fibres or rigid fibres such as polyimideamide fibres, for instance those sold under the names Kermel® and Kermel Tech® by the company Rhodia or poly(p-phenyleneterephthalamide) (or aramid) fibres sold especially under the name Kevlar® by the company DuPont de Nemours.

The fibres may be present in a composition according to the invention in a content ranging from 0.01% to 10% by weight, in particular from 0.1% to 5% by weight and more particularly from 0.3% to 3% by weight relative to the total weight of the composition.

Cosmetic Active Agents

A composition according to the invention may furthermore comprise any ingredient conventionally used in cosmetics. These ingredients may be chosen especially from polymers, especially fixing polymers; hair-conditioning agents; opacifiers; fragrances; thickeners; gelling agents; hair dyes; silicone resins; silicone gums; preserving agents; antioxidants; cosmetic active agents; sunscreens; pH stabilizers; vitamins; moisturizers; antiperspirants; deodorants; self-tanning compounds, and mixtures thereof. The amounts of these various ingredients are those conventionally used in the fields under consideration, for example from 0.01% to 20% of the total weight of the composition.

Formulation

A composition according to the invention may be in liquid, pasty, solid, mousse or spray form.

The compositions according to the invention may be used for making up human skin, lips and/or keratin fibres. These compositions thus find a particular application as body or facial makeup compositions such as foundations, lipsticks, lipcare products, nail varnishes, nailcare products, mascaras or eyeliners; haircare compositions such as hair dye compositions or antisun compositions; rinse-out compositions to be applied before or after dyeing, bleaching, permanent-waving or relaxing the hair or alternatively between the two steps of a permanent-waving or hair-relaxing operation; haircare compositions for holding the hairstyle, such as styling lacquers, gels, mousses or sprays.

According to one preferred aspect of the invention, the composition is in the form of lipsticks or complexion products, especially of the foundation type, or alternatively mascaras.

Process

In all cases, the compositions according to the invention may be prepared according to methods known to those skilled in the art.

In the case of a composition for making up keratin fibres, the process for preparing the compositions according to the invention depends on the desired type of mascara. It may also depend in particular on the nature of the wax(es) possibly used.

Another subject of the present invention is a process for making up keratin fibres, in which a composition in accordance with the invention is applied to the said keratin fibres, especially the eyelashes.

The compositions of the invention may in particular be applied to the eyelashes using a brush or a comb.

The thickening effect of the makeup, using a composition of the invention, may moreover be reinforced by most particularly selecting the device for applying the said composition.

In the present case, it is particularly advantageous, in the case of making up the eyelashes, to apply the said composition with a makeup brush as described in patents FR 2 701 198, FR 2 605 505, EP 792 603 and EP 663 161.

A composition according to the invention may be packaged in a container delimiting at least one compartment that comprises the said composition, the said container being closed by a closing member.

The container is preferably associated with an applicator, especially in the form of a brush comprising an arrangement of bristles maintained by a twisted wire. Such a twisted brush is especially described in U.S. Pat. No. 4,887,622. It may also be in the form of a comb comprising a plurality of application members, obtained especially by moulding. Such combs are described, for example, in patent FR 2 796 529. The applicator may be solidly attached to the container; as described, for example, in patent FR 2 761 959. Advantageously, the applicator is solidly attached to a stem, which is itself solidly attached to the closing member.

The closing member may be coupled to the container by screwing. Alternatively, the coupling between the closing member and the container takes place other than by screwing, especially via a bayonet mechanism, by click-fastening or by tightening. The term "click-fastening" in particular means any system involving the passing of a rim or bead of material by elastic deformation of a portion, especially of the closing member, followed by return to the elastically unstressed position of the said portion after the rim or bead has been passed.

The container may be at least partly made of thermoplastic material. Examples of thermoplastic materials that may be mentioned include polypropylene and polyethylene.

Alternatively, the container is made of a non-thermoplastic material, especially of glass or metal (or alloy).

The container is preferably equipped with a drainer located in the region of the aperture of the container. Such a drainer makes it possible to wipe the applicator and, optionally, the stem to which it may be solidly attached. Such a drainer is described, for example, in patent FR 2 792 618.

The content of the patents or patent applications mentioned previously are incorporated by reference into the present patent application.

The examples that follow are presented as non-limiting illustrations of the invention. Unless otherwise indicated, the amounts are given in grams.

The tests that follow were used to evaluate the waterproof nature and the makeup removal.

I—Test for Evaluating the Waterproof Nature and the Makeup Removal by Immersion

Specimen and Makeup Application

False eyelash specimens were made with straight black Caucasian hair with a fringe length of 19 mm. The said fringes were mounted between two 30 mm by 30 mm plates.

The hair was made up with the test composition by effecting three times ten sweeps, separated by an interval of two minutes, using a mascara brush.

The composition was left to dry for one hour at room temperature (25° C.).

Description of the Test

The specimen was immersed in water for four minutes. The appearance of degradation of the film (swelling, irregularity, detachment, etc.) was observed visually, and the time corresponding to the start of this phenomenon was noted.

II—Test for Evaluating the Makeup Removal on Dry Cotton

The specimen used for test I described above was then pinched in a piece of cotton for ten seconds, and the cotton was then drawn to remove the makeup from the said specimen. The efficacy of the makeup removal was then noted by evaluating the amount of mascara on the cotton and on the eyelashes.

Example 1

Mascara

Formulations with a high content of latex are prepared and tested. The results are collated in Table 1 below.

It is found that Tests 4 and 5, which relate to compositions according to the invention comprising both a nonionic surfactant with an HLB of greater than 10 and a polyelectrolyte, present better makeup-removing results than the Comparative Tests 1 to 3.

| Mascara | weight % |
|---|---|
| Carnauba wax (melting point: 83-86° C.) | 3.5 |
| Aliphatic polyurethane in aqueous dispersion (Avalure UR 450 ® from Noveon) | 7.6 AM* |
| Acrylamide/Na AMPS copolymer in isohexadecane with polysorbate 80 (Simulgel 600 ® from SEPPIC) | 2.5 |
| Oxyethylenated (200 EO) glyceryl monostearate (Simulsol 220 TM from SEPPIC) | 4 |
| Beeswax | 7.4 |
| Simethicone | 0.1 |
| Polyimide-amide fibres (Kermel Tech, 2 Dtex, 2 mm from Kermel) | 1 |
| Disodium EDTA | 0.2 |
| Black iron oxide | 7 |
| Butylene glycol | 5 |
| Ethanol | 3 |
| Sodium dehydroacetate | 0.2 |
| Water | qs 100 |

*AM = active material

| Mascara | weight % |
|---|---|
| Carnauba wax | 3.5 |
| Acrylic and styrene/acrylic copolymer in aqueous dispersion (Syntran 5760) | 8.0 AM* |
| Acrylamide/Na AMPS copolymer in isohexadecane (Simulgel 600) | 3.5 |
| Oxyethylenated (200 EO) glyceryl monostearate (Simulsol 220 TM from SEPPIC) | 4 |
| Beeswax | 7.4 |
| Simethicone | 0.1 |
| Fibres of rayone | 1.0 |
| Disodium EDTA | 0.2 |
| Black iron oxide | 7 |
| Butylene glycol | 5 |
| Ethanol | 3 |
| Sodium deshydroacetate | 0.2 |
| Preservatives | qs |
| Water | qs 100 |

*AM = active material

Although the present invention herein has been described with reference to particular embodiments, it is to be understood that these embodiments are merely illustrative of the principles and applications of the present invention. It is therefore to be understood that numerous modifications may be made to the illustrative embodiments and that other

TABLE 1

| | 1 (comparative) | 2 (comparative) | 3 (comparative) | 4 (invention) | 5 (invention) |
|---|---|---|---|---|---|
| Water | 57.1 | 55.1 | 56.6 | 54.6 | 52.6 |
| Syntran 5760 ®: Acrylic latex | 30 | 30 | 30 | 30 | 30 |
| Hydroxyethylcellulose | 0.9 | 0.9 | 0.9 | 0.9 | 0.9 |
| Propylene glycol | 5 | 5 | 5 | 5 | 5 |
| Black pigment | 7 | 7 | 7 | 7 | 7 |
| Cosmedia SP ® | | | 0.5 | 0.5 | 0.5 |
| Polysorbate 80 | | 2 | | 2 | 4 |
| Behaviour in water after immersion in water after 15 minutes (test I) | NTR | NTR | NTR | NTR | NTR |
| Makeup-removing behaviour after pinching/drawing once on dry cotton after 15 minutes (test II) | Light transfer onto the cotton | Light transfer onto the cotton | Very light transfer onto the cotton | ALMOST TOTAL makeup removal | TOTAL makeup removal |

NTR: Nothing to report arrangements may be devised without departing from the spirit and scope of the present invention as defined by the appended claims.

What is claimed is:

1. Mascara, said mascara having an aqueous continuous phase and comprising:
    at least one aqueous dispersion of particles of a polymer obtained by polymerization or copolymerization of monomers selected from the group consisting of styrene, vinyl acetate, urethanes, acrylic acid, methacrylic acid, and crotonic acid,
    at least one acrylamide/sodium 2-methyl-2-[(1-oxo-2-propenyl)amino]-1-propanesulfonate copolymer polyelectrolyte, which is different from the polymer in aqueous dispersion, in a solids content of greater than 1% by weight relative to the total weight of the composition, and
    at least one surfactant with an HLB of greater than or equal to 6, wherein
    said polymer is present in a solids content of greater than or equal to 5% by weight relative to the total weight of the composition, and
    a weight content of the surfactant is from 0.1% to 15%, relative to a total weight of the composition,
    said mascara forming a film when applied, and said film being able to be totally removed by mechanical rupture of the film.

2. Mascara according to claim 1, wherein the polyelectrolyte is branched and/or crosslinked.

3. Mascara according to claim 1, wherein the surfactant is selected from the group consisting of oxyethylenated and/or oxypropylenated glycerol ethers, oxyethylenated and/or oxypropylenated fatty alcohol ethers, fatty acid esters of polyethylene glycol, oxyethylenated and/or oxypropylenated fatty acid esters of glycerol ethers, oxyethylenated and/or oxypropylenated fatty acid esters of sorbitol ethers, dimethicone copolyol, dimethicone copolyol benzoate, copolymers of propylene oxide and of ethylene oxide, silicone surfactants, amino acid derivatives, $C_{16}$-$C_{30}$ fatty acid salts, polyoxyethylenated fatty acid salts, phosphoric esters and salts thereof, sulfosuccinates, alkyl ether sulfates, isethionates, acylglutamates, alkyl-imidazolidiniums, ammonium salts, and mixtures thereof.

4. Mascara according to claim 1, wherein the polymer is selected from the group consisting of synthetic polycondensate polymers, free-radical polymers, and mixtures thereof.

5. Mascara according to claim 4, wherein the free-radical polymers are acrylic and/or vinyl polymers or copolymers, acrylic/silicone copolymers or nitrocellulose/acrylic copolymers, or alternatively hybrid polymers.

6. Mascara according to claim 1, wherein the solids content of the aqueous dispersion of particles of a polymer is greater than or equal to 7% and less than 50%, relative to the total weight of the composition.

7. Mascara according to claim 1, further comprising a salt having a molar mass of less than or equal to 5000 g/mol and selected from the group consisting of EDTA, sodium dehydroacetate, NaCl, KCl, $CuSO_4$, $MgCl_2$, NaOH and $Na_2SO_4$.

8. Mascara according to claim 1, further comprising at least one oil.

9. Mascara according to claim 8, wherein an amount of the oil ranges from 1% to 30% by weight relative to the total weight of the composition.

10. Mascara according to claim 8, wherein the oil(s) present in the composition are selected from the group consisting of volatile oils, non-volatile oils, and mixtures thereof.

11. Mascara according to claim 10, wherein the volatile oils are hydrocarbon-based oils, silicone oils or fluoro oils, or mixtures thereof.

12. Mascara according to claim 1, further comprising a structuring agent.

13. Mascara according to claim 1, further comprising a film-forming polymer.

14. Mascara according to claim 1, further comprising dyestuff, fillers and/or fibers.

15. Mascara according to claim 1, wherein the polymer does not comprise an ionizable monomer.

16. Mascara according to claim 1, wherein the mascara is applied to eyelashes.

17. Mascara according to claim 1, wherein the solids content of the aqueous dispersion of particles of a polymer is greater than or equal to 7%, relative to the total weight of the composition.

* * * * *